United States Patent
Barega

(10) Patent No.: US 12,017,203 B2
(45) Date of Patent: Jun. 25, 2024

(54) METHOD FOR REMOVING A DEGRADED COMPONENT FROM A HYDROCARBON FLUID AND A POROUS MEDIUM FOR ACHIEVING THE SAME

(71) Applicant: Indufil BV, Duiven (NL)

(72) Inventor: Esayas Barega, Hydrograff (NL)

(73) Assignee: INDUFIL BV, Duiven (NL)

( * ) Notice: Subject to any disclaimer, the term of this patent is extended or adjusted under 35 U.S.C. 154(b) by 359 days.

(21) Appl. No.: 15/930,902

(22) Filed: May 13, 2020

(65) Prior Publication Data

US 2020/0360893 A1 Nov. 19, 2020

Related U.S. Application Data

(60) Provisional application No. 62/846,858, filed on May 13, 2019, provisional application No. 62/925,266, filed on Oct. 24, 2019.

(30) Foreign Application Priority Data

Oct. 4, 2019 (GB) ..................................... 1914383

(51) Int. Cl.
*B01D 39/04* (2006.01)
*B01D 46/00* (2022.01)
(Continued)

(52) U.S. Cl.
CPC ........ *B01J 20/267* (2013.01); *B01D 46/0036* (2013.01); *B01J 20/261* (2013.01);
(Continued)

(58) Field of Classification Search
CPC ................ B01D 39/04; B01D 46/0036; B01D 2239/1216; B01D 2239/1241;
(Continued)

(56) References Cited

U.S. PATENT DOCUMENTS 3,594,983 A * 7/1971 Yearout ................ B01D 53/047
95/122
3,632,504 A * 1/1972 Name not available ....................
C10G 5/02
95/143

(Continued)

FOREIGN PATENT DOCUMENTS

CN 102093499 A 6/2011
CN 108355626 A 8/2018
(Continued)

OTHER PUBLICATIONS

Abstract of CN102093499A, 1 pg.
(Continued)

*Primary Examiner* — Frank M Lawrence, Jr.
(74) *Attorney, Agent, or Firm* — CANTOR COLBURN LLP

(57) ABSTRACT

A method of removing a degraded component from a hydrocarbon fluid includes: receiving the hydrocarbon fluid from a fluid source; directing the hydrocarbon fluid to a first porous medium capable of adsorbing the degraded component to produce a purified fluid that has a reduced amount of degraded component as compared to the hydrocarbon fluid; removing the purified fluid from the first porous medium; and regenerating the first porous medium with a regenerant. The porous medium can include a crosslinked polystyrene having at least one of a BET pore volume of greater than or equal to 0.6 mL/g or a surface area of 500 to 900 $m^2/g$, or 500 to 850 $m^2/g$ as determined in accordance with to ISO 9277:2010.

14 Claims, 2 Drawing Sheets

(51) Int. Cl.
  *B01J 20/20* (2006.01)
  *B01J 20/26* (2006.01)
  *B01J 20/28* (2006.01)
  *B01J 20/34* (2006.01)
  *C07C 7/12* (2006.01)

(52) U.S. Cl.
  CPC ... *B01J 20/28064* (2013.01); *B01J 20/28073* (2013.01); *B01J 20/28083* (2013.01); *B01J 20/3425* (2013.01); *C07C 7/12* (2013.01)

(58) Field of Classification Search
  CPC ... B01D 53/04; C07C 7/12; C07C 7/13; B01J 20/18; B01J 20/20; B01J 20/261; B01J 20/267; B01J 20/28064; B01J 20/28069; B01J 20/28073; B01J 20/2808; B01J 20/28083; B01J 20/3425; B01J 20/3475
  USPC .......... 210/690, 660, 670, 674, 263; 96/108, 96/121; 95/141; 502/402; 585/820
  See application file for complete search history.

(56) References Cited

U.S. PATENT DOCUMENTS

| | | | |
|---|---|---|---|
| 4,233,038 A * | 11/1980 | Tao | B01D 53/04 |
| | | | 95/139 |
| 5,401,393 A * | 3/1995 | Whitehurst | C10G 25/02 |
| | | | 502/402 |
| 5,906,675 A * | 5/1999 | Jain | F25J 3/04163 |
| | | | 95/143 |
| 5,976,221 A | 11/1999 | Bowman et al. | |
| 5,980,612 A * | 11/1999 | Kelly | B01J 20/3441 |
| | | | 95/114 |
| 8,753,014 B2 | 6/2014 | Devitt | |
| 9,441,668 B2 | 9/2016 | Devitt | |
| 10,030,666 B2 | 7/2018 | Devitt | |
| 10,100,932 B2 | 10/2018 | Devitt | |
| 2003/0027879 A1 * | 2/2003 | Davankov | B01J 20/261 |
| | | | 521/82 |
| 2009/0001023 A1 | 1/2009 | Dufresne et al. | |
| 2011/0089114 A1 | 4/2011 | Livingstone et al. | |
| 2012/0090465 A1 * | 4/2012 | Winter | B01D 53/0476 |
| | | | 95/96 |
| 2014/0286599 A1 | 9/2014 | Devitt et al. | |
| 2015/0290575 A1 * | 10/2015 | Rothermel | B01D 53/0423 |
| | | | 703/1 |
| 2019/0049019 A1 | 2/2019 | Devitt | |

FOREIGN PATENT DOCUMENTS

| | | |
|---|---|---|
| EP | 2138230 A2 | 12/2009 |
| IN | 106861236 A | 6/2017 |
| WO | 2008108738 A1 | 2/2008 |
| WO | 2013115634 A1 | 8/2013 |
| WO | 2015130338 A1 | 9/2015 |
| WO | 2016191259 A1 | 12/2016 |
| WO | 2016205444 A1 | 12/2016 |
| WO | 2017178593 A2 | 10/2017 |
| WO | 2017178593 A3 | 10/2017 |
| WO | 2019023350 A1 | 1/2019 |
| WO | 2019032283 A1 | 2/2019 |
| WO | 2019072105 A1 | 4/2019 |

OTHER PUBLICATIONS

Abstract of CN106861236A, 2 pages.
Abstract of CN108355626A, 2 pages.
Combined Search and Examination Report for International Application No. GB1914383.3 dated Dec. 18, 2019 10 pages.
Combined Search and Examination Report for International Application No. GB2007083.5 dated Aug. 26, 2020, 11 pages.
PCT International Search Report and Written Opinion for International Application No. PCT/EP2020/063386, dated Jul. 17, 2020, 12 pages.

* cited by examiner

METHOD FOR REMOVING A DEGRADED COMPONENT FROM A HYDROCARBON FLUID AND A POROUS MEDIUM FOR ACHIEVING THE SAME

CROSS REFERENCE TO RELATED APPLICATION

This application claims the benefit of an earlier filing date from U.S. Provisional Application Ser. No. 62/846,858 filed May 13, 2019; UK Patent Application No. 1914383.3 filed Oct. 4, 2019; and U.S. Patent Application No. 62/925,266 filed Oct. 24, 2019, the entire disclosures of which are incorporated herein by reference.

BACKGROUND

Hydrocarbon fluids can undergo various stresses in lubricating processes that can cause them to degrade. This degradation results in the formation of less soluble degraded components that can be either dissolved or suspended depending upon the chemistry and temperature of the hydrocarbon fluid. When the degraded components are in a suspended state, they can settle out of solution and can disadvantageously form deposits, often referred to as varnish, in the system. The formation of the varnish can be significant, especially in cooler sections or in low-flow sections of lubrication systems and can form significant build-up on infrequently used components such as servo-valves risking their performance, reliability, or safety of the entire system.

While technologies, such as electrostatic oil cleaning and depth media filters, have been developed to remove these components, they have only achieved moderate success. Therefore, improved methods of removing the degradation components are desired.

BRIEF SUMMARY

Disclosed herein is a method for removing a degraded component from a hydrocarbon fluid and a porous medium for achieving the same.

In one embodiment, a porous medium for removing a degraded component from a hydrocarbon fluid is disclosed. The porous medium can comprise a crosslinked polystyrene having at least one of a BET pore volume of greater than or equal to 0.6 mL/g or a surface area of 500 to 900 m$^2$/g, or 500 to 850 m$^2$/g as determined in accordance with to ISO 9277:2010.

In the prior porous medium embodiment, the porous medium can be non-ionic and can be free of both a cationic and an anionic functionality.

In any of the prior porous medium embodiments, the porous medium can have an average pore size of 5 to 18 nanometers.

In another embodiment, a method of removing a degraded component from a hydrocarbon fluid comprises receiving the hydrocarbon fluid from a fluid source; directing the hydrocarbon fluid to a first porous medium capable of adsorbing the degraded component to produce a purified fluid that has a reduced amount of degraded component as compared to the hydrocarbon fluid; removing the purified fluid from the first porous medium; and regenerating the first porous medium with a regenerant.

In the prior method embodiment of removing a degraded component, the directing the hydrocarbon fluid to the first porous medium can comprise directing a hydrocarbon fluid stream to a first filter section comprising the first porous medium produce a purified stream comprising the purified fluid. The removing the purified fluid from the first porous medium can comprise directing a flow of the purified stream from the first filter section. The method can further comprise stopping a flow of the hydrocarbon fluid stream to the first filter section after an amount of time and directing the hydrocarbon fluid stream to a second filter section comprising a second porous medium capable of adsorbing the degraded component to produce the purified stream. The regenerating the first porous medium can comprise introducing the regenerant to the first filter section to remove an amount of the degraded component from the first porous medium.

In the prior method embodiment of removing a degraded component, the introducing the regenerant to the first filter section can comprise directing a first regenerant stream comprising the regenerant to the first filter section and removing a degraded component removal stream from the first filter section.

In the prior method embodiment of removing a degraded component, the method can comprise stopping the flow of the regenerant stream to the first filter section after an amount of the degraded component is removed from the first filter section and then re-initiating a flow of the hydrocarbon fluid stream to the first filter section to produce the purified stream.

In any of the prior three method embodiments of removing a degraded component, the method can comprise stopping a flow of the hydrocarbon fluid stream to the second filter section and directing the hydrocarbon fluid stream to a third filter section comprising a third porous medium capable of adsorbing the degraded component to produce the purified stream. After stopping the flow of the hydrocarbon fluid stream to the second filter section, a second regenerant stream can be directed to the second filter section to remove the degraded component from the second porous medium.

In any of the prior method embodiments of removing a degraded component, the introducing regenerant to the first porous medium can comprise removing the first porous medium located in a first filter location and introducing the regenerant to the first porous medium in a second location different from the first location. The first porous medium can be replaced to the first filter location after the amount of the degraded component is removed from the first porous medium.

In any of the prior method embodiments of removing a degraded component, the first porous medium and the second porous medium can each independently have a porosity and the first porous medium and the second porous medium can each independently comprise at least one of cotton, activated carbon, a zeolite, or a crosslinked polymeric material.

In any of the prior method embodiments of removing a degraded component, the first porous medium and the second porous medium can each independently be present in an amount greater than 0.5 grams of the respective porous medium per 110 milliliters of the hydrocarbon fluid stream.

In any of the prior method embodiments of removing a degraded component, a solid particulate prefilter can be located upstream of at least one of the first porous medium or the second porous medium.

In any of the prior method embodiments of removing a degraded component, at least one of the first porous medium or the second porous medium can comprise a crosslinked polystyrene having a BET pore volume of greater than or equal to 0.6 mL/g and a surface area of 500 to 900 m²/g, or 500 to 850 m²/g as determined in accordance with to ISO 9277:2010.

In any of the prior method embodiments of removing a degraded component, at least one of the first porous medium or the second porous medium can be non-ionic and can be free of both a cationic and an anionic functionality.

In any of the prior method embodiments of removing a degraded component, at least one of the first porous medium or the second porous medium can have an average pore size of 5 to 18 nanometers.

In yet another embodiment, a method of regenerating a porous medium comprising a degraded component comprises introducing a regenerant to the porous medium for an amount of time sufficient to remove at least a portion of the degraded component. The porous medium can comprise at least one of a crosslinked polystyrene or an acrylic resin. The regenerant can comprise at least one of acetone, methanol, ethanol, propanol, or butanol.

In any of the prior method embodiments of regenerating a porous medium, the porous medium can be present in an amount of greater than 0.5 grams of the porous medium per 110 milliliters of the hydrocarbon fluid.

In any of the prior method embodiments of regenerating a porous medium, the porous medium can comprise a crosslinked polystyrene having a BET pore volume of greater than or equal to 0.6 mL/g and a surface area of 500 to 900 m²/g, 500 to 850 m²/g as determined in accordance with to ISO 9277:2010.

In any of the prior method embodiments of regenerating a porous medium, the porous medium can be non-ionic and can be free of both a cationic and an anionic functionality.

In any of the prior method embodiments of regenerating a porous medium, the porous medium can have an average pore size of 5 to 18 nanometers.

In another embodiment, a facility for removing a degraded component from a hydrocarbon fluid comprises a first filter section in fluid communication with a hydrocarbon fluid stream for receiving the hydrocarbon fluid and a purified stream for removing a purified hydrocarbon fluid; wherein the first filter section comprises a first porous medium capable of removing a degraded component from the hydrocarbon fluid; and a second filter section in fluid communication with the hydrocarbon fluid stream for receiving the hydrocarbon fluid and the purified stream for removing the purified hydrocarbon fluid; wherein the second filter section comprises a second porous medium capable of removing a degraded component from the hydrocarbon fluid. At least one of the first filter section and the second filter section can be in fluid communication with a regenerant stream for receiving a regenerant and a degraded component removal stream for removing a degraded component; or the first porous medium and the second porous medium can be capable of being removed from the respective filter locations.

In the prior embodiment of the facility, the facility can comprise at least one of a filter section valve capable of diverting a flow of the hydrocarbon stream between the first filter section and the second filter section or a regenerant direction valve capable of diverting a flow of the regenerant stream between the first filter section and the second filter section.

In any of the prior facility embodiments, the facility can comprise a third filter section in fluid communication with the hydrocarbon fluid stream for receiving the hydrocarbon fluid and the purified stream for removing the purified hydrocarbon fluid. The third filter section can comprise a third porous medium capable of removing a degraded component from the hydrocarbon fluid.

In any of the prior facility embodiments, at least one of the first porous medium, the second porous medium, or the third porous medium can comprise a crosslinked polystyrene.

The above described and other features are exemplified by the following figures, detailed description, and claims.

BRIEF DESCRIPTION OF THE DRAWINGS

The following figures are exemplary embodiments, which are provided to illustrate the present disclosure. Some of the figures are illustrative of the examples, which are not intended to limit devices made in accordance with the disclosure to the materials, conditions, or process parameters set forth herein.

DETAILED DESCRIPTION

Figure 1:
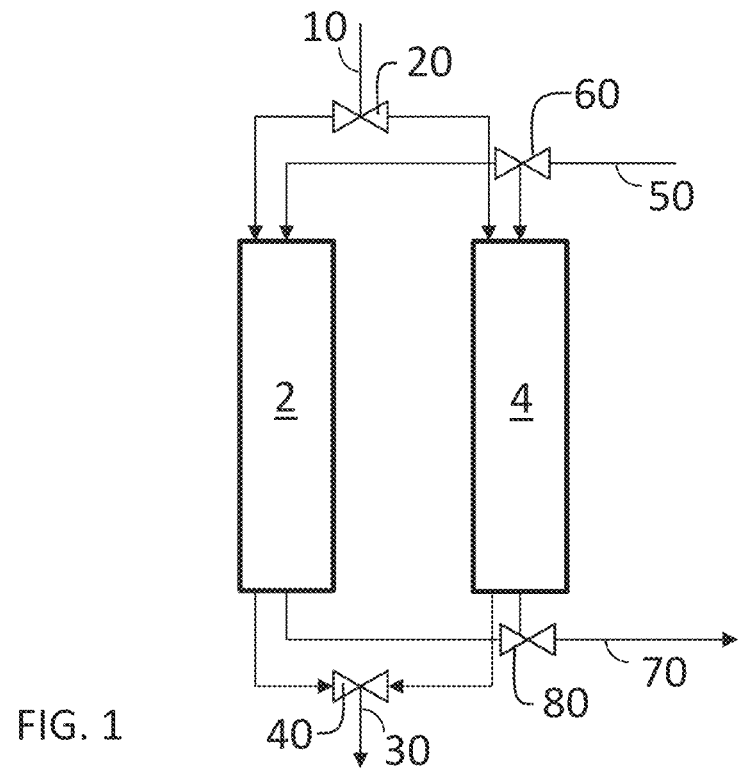
FIG. 1 is an illustration of system that can be utilized to remove a degraded component and regenerate a hydrocarbon fluid.

Disclosed herein is a porous medium for removing a degraded component from a hydrocarbon fluid that exhibits significant improvements in reducing the varnish potential and a method for regenerating the same. Also disclosed herein is an improved process for removing a degraded component from a hydrocarbon fluid. Utilizing one or both of the porous medium or the improved process removing a degraded component from a hydrocarbon fluid can significantly increase the lifetime of the hydrocarbon fluid and can reduce the contamination of components in a lubricating system.

The porous medium can comprise a crosslinked polystyrene having at least one of a pore volume of greater than or equal to 0.6 milliliters per gram (mL/g) as determined using the Brunauer-Emmet-Teller (BET) method using nitrogen adsorption at 77 Kelvin; or a surface area of 500 to 900 meters squared per gram (m²/g), or 500 to 850 m²/g as determined in accordance within accordance with to ISO 9277:2010. The crosslinked polystyrene was found to be capable of adsorbing a surprising amount of degraded components, for example, including both soluble and insoluble oil oxidation by-products (such as polar byproducts resulting from degradation, such as hydrocarbon degradation) to extend the life of the hydrocarbon fluid. The crosslinked polystyrene can have an improved adsorbent capacity, for example, achieving a membrane patch colorimetry (MPC) value of less than 15 color units (dE), or less than or equal to 10 dE, or 5 to 10 dE as determined in accordance with ASTM D7843-18.

In general, membrane patch colorimetry mixes a sample of the hydrocarbon fluid with a solvent to accelerate the precipitation of a degradation component and then filters the mixture through a membrane patch. The color of the patch is analyzed with a spectrophotometer, where the darker the color of the patch, the more severe the varnish potential. The industry standard for acceptable MPC values directs that a sample having a MPC value of less than 15 dE indicates a clean sample, an MPC value of 15 to 25 dE indicates an acceptable degraded component level, an MPC value of 25 to 35 dE indicates a somewhat high degraded component level, and an MPC value of greater than 35 dE indicates an unacceptable degraded component level.

The crosslinked polystyrene can be derived from at least a styrene monomer and a crosslinker. The styrene monomer can comprise one or both of styrene or a substituted styrene monomer (for example, alpha-methyl styrene, vinyl toluene, ethyl vinyl benzene, isopropenyl toluene, vinyl xylene, or vinyl naphthalene). The styrene monomer can comprise a halogenated styrene such as vinylbenzyl chloride. The crosslinked polystyrene can comprise repeat units derived from acrylonitrile, for example, comprising 1 to 4 mole percent of repeat units derived from acrylonitrile based on the total moles of repeat units of the crosslinked polystyrene.

The crosslinker can comprise at least one of divinyl benzene, divinyl toluene, trivinyl benzene, divinyl chloro benzene, diallyl phthalate, divinyl naphthalene, divinyl xylene, divinyl ethyl benzene, divinyl pyridine, divinyl sulfone, divinyl ketone, divinyl sulfide, ethylene glycol diacrylate, ethylene glycol dimethacrylate, trimethylol propane trimethacrylate, neopentyl glycol dimethacrylate, bisphenol A dimethacrylate, pentaerythritol tetramethacrylate, pentaerythritol trimethacrylate, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, N,N'-methylene diacrylamide, N,N'-methylene dimethacrylamide, N,N'-ethylene diacrylamide, trivinyl naphthalene, or polyvinyl anthracene. The crosslinker can comprise at least one of divinyl benzene, divinyl toluene, trivinyl benzene, divinyl chloro benzene, diallyl phthalate, divinyl naphthalene, divinyl xylene, or divinyl ethyl benzene. The amount of the crosslinker can vary, but can be present in an amount sufficient to produce the crosslinked polystyrene having the desired pore volume or surface area.

The crosslinked polystyrene can be non-ionic, being free of both a cationic and an anionic functionality. In other words, the crosslinked polystyrene can be free of an ion exchange ability, which can help to avoid the release of water into the oil as a result of ion-exchange reaction for amine functionalized resins.

The crosslinked polystyrene can have a pore volume of greater than or equal to 0.6 mL/g, or 0.6 to 2 mL/g, or 0.75 to 1.5 mL/g as determined using the BET method using nitrogen adsorption at 77 Kelvin. The crosslinked polystyrene can have a surface area of 500 to 900 m$^2$/g, or 500 to 850 m$^2$/g, or 600 to 850 m$^2$/g as determined in accordance with ISO 9277:2010. The crosslinked polystyrene can have an average pore size of 5 to 18 nanometers that can be determined using mercury porosimetry. The crosslinked polystyrene can be in the form of a plurality of beads or a porous plug. When in the form of beads, the bead size can have a mesh size of 16 to 50.

After an amount of time, the effectiveness of the porous medium (for example, comprising at least one of the crosslinked polystyrene or an acrylic resin) will decrease as more and more of the degraded component is adsorbed onto the surface. A method of regenerating the porous medium comprising an adsorbed degraded component was also developed. The method comprises introducing a regenerant to the porous medium for an amount of time sufficient to remove at least a portion of the degraded component. During the introducing, the porous medium can be present in an amount of greater than 0.5 grams of the porous medium per 110 milliliters of the regenerant. The introducing can occur at a temperature of 35 to 70 degrees Celsius (° C.), or 40 to 60° C.

The regenerant can comprise at least one of acetone, methanol, ethanol, propanol, butanol (for example, isobutanol), methyl acetate, ethyl acetate, a terpene, acetonitrile, dioxane, acetic acid, formic acid, chloroform, tetrahydrofuran, dimethylformamide, dimethyl sulfoxide, methyl ethyl ketone (MEK), methyl propyl ketone, methyl iso-amyl ketone, methyl iso-butyl ketone (MIBK), methyl oleate, methyl propyl ketone, n-methyl-2-pyrrolidone (NMP), n-propyl acetate, n-propyl propanoate, propylene glycol monobutyl ether, propylene glycol monoethylene ether acetate, propylene glycol monomethyl ether acetate, toluene, xylene, benzene, iso-pentyl acetate, iso-pentyl alcohol, iso-butyl isobutyrate, n-amyl acetate, n-amyl alcohol, benzyl alcohol, N—N-dimethyl formamide (DMF), n-propyl acetate, n-propyl propanoate, sulfolane, 1-nitro propane, sec-butyl acetate, methyl cellosolve, methyl carbitol, or methyl iso-butyl carbinol. The regenerant can comprise at least one of acetone, methanol, ethanol, propanol, or butanol.

An improved process for removing a degraded component from a hydrocarbon fluid was also developed. The method comprises receiving the hydrocarbon fluid from a fluid source; directing the hydrocarbon fluid to a first porous medium capable of adsorbing the degraded component to produce a purified fluid that has a reduced amount of degraded component as compared to the hydrocarbon fluid; removing the purified fluid from the first porous medium; and regenerating the first porous medium with a regenerant. It is noted that this method can successfully remove a degraded component from a hydrocarbon fluid using variety of porous medium and is not limited to merely utilizing a crosslinked polystyrene. For example, the porous medium can comprise at least one of cotton, activated carbon, a zeolite, or a crosslinked polymeric material (for example, a crosslinked polystyrene or an acrylic resin).

An example of a method of removing a degraded component is illustrated in FIG. 1. FIG. 1 illustrates that a hydrocarbon fluid stream 10 can be directed to a first filter section 2 comprising a first porous medium to produce a purified stream 30 comprising a purified fluid. The purified fluid can be removed from the first porous medium by directing a flow of the purified stream 30 from the first filter section 2. With time, the adsorptive capability of the first porous medium will naturally decrease as increasing amounts of the degraded component is adsorbed onto the surface. This change in adsorptive capability can be monitored, for example, by determining the MPC values of the hydrocarbon fluid stream 10 with time or via an inline measurement technique, for example, by determining the total acid number of the hydrocarbon fluid. Therefore, after an amount of time, the flow of the hydrocarbon fluid stream 10 to the first filter section 2 can be stopped and the flow of the hydrocarbon fluid stream 10 can be redirected to a second filter section 4 comprising a second porous medium capable of adsorbing the degraded component to produce the purified stream 30. FIG. 1 illustrates that the flow of the hydrocarbon fluid stream 10 can be redirected from first filter section 2 to the second filter section 4 using a three-way valve 10 and the purified stream 30 can be directed from the respective sections via a purified stream valve 40. It is noted that the valve configurations presented in the figures are not to be considered limiting and are merely presented as illustrative embodiments.

While the flow of the hydrocarbon fluid stream 10 is being directed to the second filter section 4, the first filter section 2 can be regenerated by directing a flow of a regenerant stream 50 to the first filter section 2. A degraded component removal stream 70 can be directed from the first filter section 2. The regeneration process can be a continuous, a semi-continuous, or a batch process. For example, the regenerant stream 50 can be added continuously and the degraded component removal stream 70 can be removed continuously to create a constant flow of the regenerant through the first filter section 2. Conversely, the regenerant stream 50 can be introduced to the first filter section 2 such that the first porous medium is rinsed with the regenerant for an amount of time, after which the degraded component removal stream 70 can be removed from the first filter section 2. Once the first porous medium has been regenerated, the flow of the hydrocarbon fluid stream 10 can be redirected back to the first filter section 2 and the regenerant stream 50 can be directed to the second filter section 4 to regenerate the second porous medium. The flow of the regenerant stream 50 can be directed to the respective filter sections using a regenerant direction valve 60 and the degraded component removal stream 70 can be directed from the respective sections via a degraded component removal valve 80. During the regenerating, a regenerant at high temperature (for example, at 35 to 70° C., or 40 to 60° C.) can be applied to the respective filter section to facilitate desorption of the degraded component into the regenerant. It is noted that depending on the maximum operating temperature of the porous medium, higher temperatures could be used.

By regenerating the porous medium in-line in the system, a reduced down time of the purification method can be observed. Additionally regeneration results in a reduced operational cost of the porous medium, which otherwise needs to replaced and disposed of. In order to reduce the likelihood of contamination of the hydrocarbon fluid with the regenerant, the porous medium can be dried by at least one of heating or gas flow through the porous medium prior to reintroduction of the hydrocarbon fluid. Likewise, the porous medium can be dried prior to the adsorption step to remove any moisture from the adsorbent.

Figure 2:
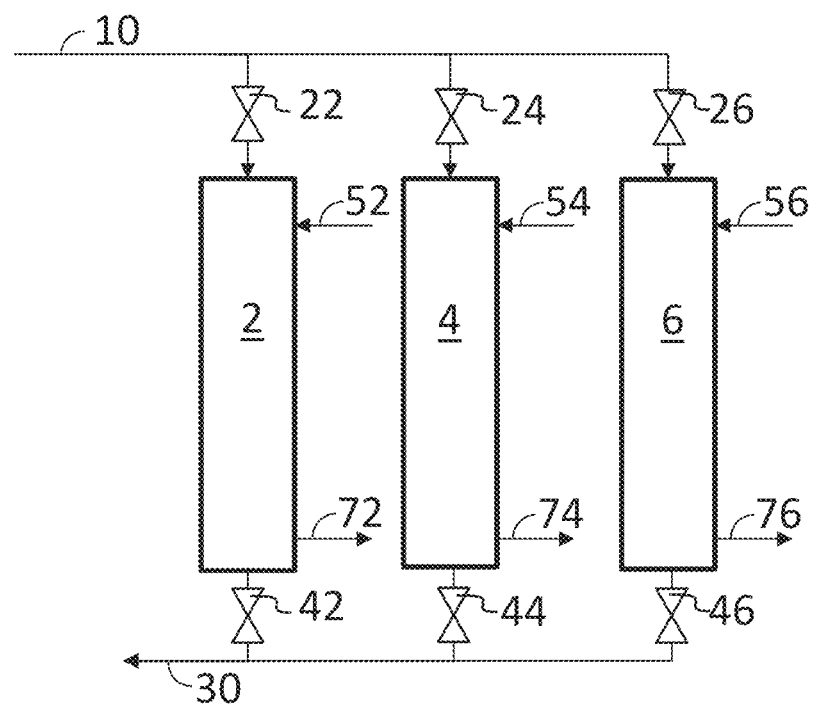
FIG. 2 is another illustration of system that can be utilized to remove a degraded component and regenerate a hydrocarbon fluid.

Depending on the relative rates of the reduction in the adsorptive ability of the porous medium and the rate of regeneration of the porous medium, different configurations of the facility are envisioned, for example, as illustrated in FIG. 2 with the addition of a third filter section 6. For example, if the regeneration rate of the porous medium is slower than the reduction rate of the adsorptive ability, then the third filter section 6 can be used to remove the degraded component from the hydrocarbon stream 10 while accommodating the longer regeneration times of the first filter section 2 and the second filter section 4. In this configuration, longer times for the regeneration of the porous medium can be accommodated without stopping the flow of the hydrocarbon fluid through a porous medium.

FIG. 2 illustrates a facility that comprises a third filter section 6 that comprises a third porous medium in addition to the first filter section 2 and the second filter section 4. In this configuration, the hydrocarbon fluid stream 10 can be directed to a first filter section 2 to produce a purified stream 30 comprising a purified fluid. The purified fluid can be removed from the first porous medium by directing a flow of the purified stream 30 from the first filter section 2. After an amount of time, the flow of the hydrocarbon fluid stream 10 to the first filter section 2 can be stopped, for example, by closing a first filter section valve 22 and the first purified stream valve 42 and the flow of the hydrocarbon fluid stream 10 can be redirected to a second filter section 4 by opening a second filter section valve 24 and the second purified stream valve 44. While the flow of the hydrocarbon fluid stream 10 is diverted from the first filter section 2, a first regenerant stream 52 can be directed to the first filter section 2 and a first removal stream 72 can be directed from the first filter section 2. After a further amount of time, the flow of the hydrocarbon fluid stream 10 to the second filter section 4 can be stopped, for example, by closing a second filter section valve 24 and the second purified stream valve 44 and the flow of the hydrocarbon fluid stream 10 can be redirected to a third filter section 6 by opening a third filter section valve 26 and the third purified stream valve 46. While the flow of the hydrocarbon fluid stream 10 is diverted from the second filter section 4, a second regenerant stream 54 can be directed to the second filter section 4 and a second removal stream 74 can be directed from the second filter section 4. Once the first filter section 2 has been regenerated, a flow of the first regenerant stream 52 can be stopped and a flow of the hydrocarbon fluid stream 10 into the first filter section 2 can be re-initiated.

Other configurations of flow through the facility of FIG. 2 are also considered. For example, if the regeneration rate of the porous medium is faster than the reduction rate of the adsorptive ability, then flow of the hydrocarbon fluid stream can occur in parallel through different porous medium, for example, with a staggered starting time and diverted independently as needed to accommodate regeneration. In this configuration, an increased amount of the hydrocarbon fluid can be purified. Considering FIG. 2 in view of this configuration, a flow of the hydrocarbon fluid stream 10 can be initiated to first filter section 2. After an amount of time, a flow of the hydrocarbon fluid stream 10 can be directed to second filter section 4, and likewise to a third filter section 6. Once the adsorptive ability is reduced in the first filter section 2 below a desired amount, the flow of the hydrocarbon fluid stream 10 to the first filter section 2 can be ceased and the flow of the first regenerant stream 52 can be initiated. After the first porous medium in the first filter section 2 is regenerated, the flow of the hydrocarbon fluid stream 10 can be reinitiated. Likewise, the flow of the hydrocarbon stream 10 to the respective filter sections can be stopped and started independently as needed for their respective regeneration steps.

In order to maintain a constant overall flow through the system of FIG. 2, the method can comprise flowing the hydrocarbon fluid stream 10 through the same number of filter sections and alternating the off-line time of the filter sections during their respective regenerating steps. For example, once the flow of the hydrocarbon fluid stream 10 to the first filter section 2 is stopped, then the flow of the hydrocarbon fluid stream 10 can be initiated in third filter section 6 such that the hydrocarbon fluid stream 10 is being filtered in both second filter section 4 and in third filter section 6. Later, once the first porous medium in the first filter section 2 is regenerated and/or the adsorptive ability of the second filter section 2 has been reduced, then the flow of the hydrocarbon fluid stream 10 to the second filter section 4 can be stopped and can be re-initiated to the first filter section 2.

While only three filter sections are illustrated in FIG. 2, it is understood that more filter sections can be added as needed or desired.

Figure 3:
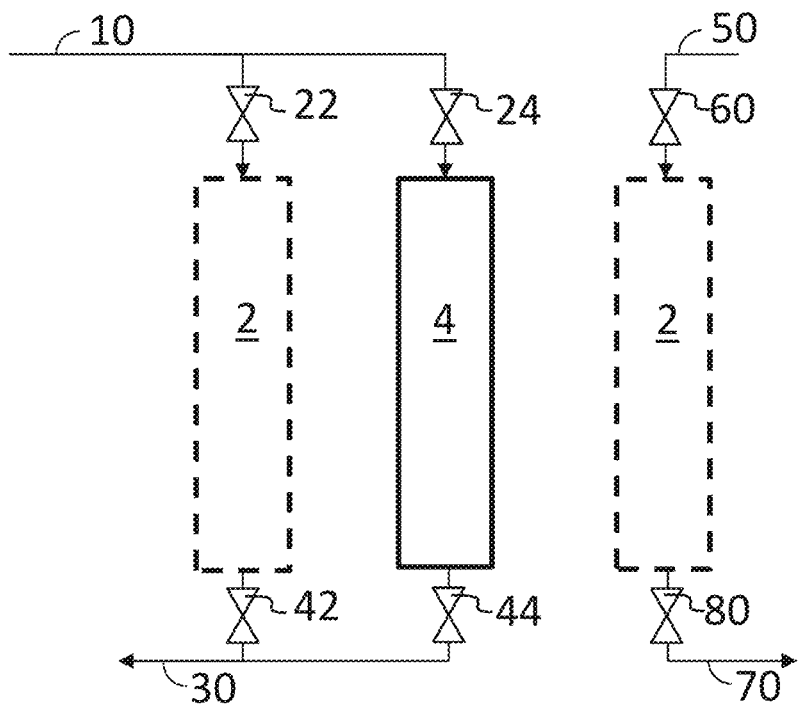
FIG. 3 is yet another illustration of system that can be utilized to remove a degraded component and regenerate a hydrocarbon fluid.

FIG. 3 illustrates that instead of regenerating the porous medium in-line, the porous medium can be regenerated off-line, by removing the porous medium from the respective filter section and regenerating the porous medium in a separate location. Specifically, FIG. 3 illustrates that once the adsorbent ability of the first porous medium in the first filter section 2 is reduced, a flow of the hydrocarbon fluid stream 10 to the first filter section 2 located in a first location can be stopped. The first porous medium can then be removed and a regenerant can be added to the first porous medium in a second location different from the first location. The regenerant can be introduced to the porous medium for an amount of time sufficient to remove at least a portion of the degraded component. FIG. 3 illustrates that the regenerant can be introduced to the porous medium via introduction of the regenerant stream 50 and removal of degraded component stream 70. The second location can be an off-site location from the first location of the hydrocarbon cleaning facility. Once the first porous medium is regenerated, it can be replaced to the first filter section 2. It is noted that removing the porous medium from the system prior to introducing the regenerant can reduce the likelihood of contamination of the hydrocarbon fluid with the regenerant.

FIG. 3 illustrates that while the first porous medium is being regenerated, the flow of the hydrocarbon fluid stream 10 can be redirected to a second filter location 4 comprising a second porous medium. This second porous medium can likewise be removed when a regeneration step is needed.

It is noted that the porous medium in the respective filter sections can be the same or different from that of respective filter sections. For example, the respective filter sections can all comprise a crosslinked polystyrene. Conversely, a first filter section can comprise a crosslinked polystyrene and a second filter section can comprise a different porous medium. The porous medium in the respective filter sections independently can be present in an amount greater than 0.5 grams of the respective porous medium per 110 milliliters of the hydrocarbon fluid stream.

The respective filter sections can comprise a solid particle prefilter, for example, located upstream of the porous medium. The solid particle prefilter can be located upstream of a regenerant introduction location such that it is does not come into physical contact with the regenerant during the regenerating or the solid particle prefilter can be located such that it does come into physical contact with the regenerant during the regenerating.

The hydrocarbon fluid can comprise at least one of a turbine oil, a lubricating oil, a hydraulic oil, a petroleum oil, gasoline, diesel fuel, or mineral oil. The hydrocarbon fluid can comprise at least one of a natural or a synthetic lubricating oil. The hydrocarbon fluid can comprise Shell Turbo GT 32 oil or Shell Turbo CC 32 turbine oil.

The following examples are provided to illustrate the present disclosure. The examples are merely illustrative and are not intended to limit devices made in accordance with the disclosure to the materials, conditions, or process parameters set forth therein.

EXAMPLES

In the examples, adsorbent capacity of various porous media was determined using MPC according to ASTM D7843-18. Specifically, a degraded component containing hydrocarbon fluid was mixed in a shaker bath at a frequency of 190 Hertz with an adsorbent for 72 hours at 50° C. to produce a purified sample. Then, 50 milliliters of purified sample were mixed with an equal volume of petroleum ether. The resulting solution was filtered through a 0.45 micrometer, 47 millimeter Nitro-Cellulose membrane and the color of the membrane was determined in the CIE LAB scale as DE (ASTM E308-18)

In the examples, the components as listed in Table 1 were used.

TABLE 1

| Adsorbent | Description | Source |
|---|---|---|
| PSDVB-2 | Amberlite ™ XAD-4, a divinyl benzene crosslinked polystyrene composition having a pore volume of 0.98 mL/g, an average pore size of 10 nm, and a surface area of 750 m$^2$/g | Sigma Aldrich |
| Acryl-3 | Amberlite ™ XAD-7, a porous acrylic composition having a pore volume of 0.5 mL/g, an average pore size of 9 nm, and a surface area of 450 m$^2$/g | Sigma Aldrich |
| PSDVB-4 | Dowex ™ 66 base, an amine functionalized divinyl benzene crosslinked polystyrene composition having exchange capacity of 1.6 mEq/mL and a particle size of 50-125 mesh | Sigma Aldrich |
| Acryl-5 | Amberlite ™ IRA-67, free base, a tertiary amine functionalized acrylic gel composition having exchange capacity of 1.6 and a particles size of no. 16 to 50 mesh | Sigma Aldrich |
| PSDVB-6 | Amberlite ™ XAD-16N, a divinyl benzene crosslinked polystyrene composition having a pore volume of 0.55 mL/g, an average pore size of 20 nm, and a surface area of 900 m$^2$/g | Sigma Aldrich |
| PSDVB-7 | Dowex ™ MB, a sulfonic acid and quaternary amine functionalized divinyl benzene crosslinked polystyrene composition having exchange capacity of 1 mEq/mL | Sigma Aldrich |
| CF-8 | Arbocel ™, cellulose fiber, with 99.5% alpha-cellulose content, having a fiber length of 700 μm, fiber thickness of 20 μm, and bulk density of 35-55 g/L | J. RETTENMAIER & SÖHNE GmbH + Co KG |
| CP-9 | Vitacel ™, cellulose powder having granulate size of 80 μm and a bulk density of 400-500 g/L | J. RETTENMAIER & SÖHNE GmbH + Co KG |

Examples 1-7: Effect of Adsorbent on Degraded Component Level 16.5 grams of an adsorbent as indicated in Table 2 were added to 110 milliliters (mL) of a Shell Turbo CC 32 turbine oil containing an amount of degraded component and having an MPC value of 65 E and a total acid number of 0.25 milligrams KOH per gram. The samples were mixed for 72 hours at 50° C. to produce a purified oil sample. The MPC values of the purified oil samples were determined and are shown in Table 2, where details of the adsorbent have been added.

TABLE 2

| Example | 1 | 2 | 3 | 4 | 5 | 6 | 7 |
|---|---|---|---|---|---|---|---|
| Adsorbent | None | PSDVB-2 | Acryl-3 | PSDVB-4 | Acryl-5 | PSDVB-6 | PSDVB-7 |
| Functionality | N/A | — | — | amine | amine | — | amine and sulfonic acid |

TABLE 2-continued

| Example | 1 | 2 | 3 | 4 | 5 | 6 | 7 |
|---|---|---|---|---|---|---|---|
| Pore size (nm) | N/A | 10 | 9 | — | — | 20 | — |
| Surface area ($m^2/g$) | N/A | 750 | 450 | — | — | 900 | — |
| Exchange Capacity (mEq/mL) | N/A | — | — | 1.6 | 1.6 | — | 1 |
| Pore volume (mL/g) | N/A | 0.98 | 0.5 | — | — | 0.55 | — |
| MPC value (dE) | 65.2 | 7.2 | 23.1 | 17.9 | 16.4 | 28.3 | 23.7 |

Table 2 shows that Example 2 resulted in a purified oil with an MPC value of only 7.2 dE.

Example 8: Effect of Adsorbent Amount on Adsorbent Ability

The adsorbent abilities with decreasing concentration of the adsorbents 2, 4, and 5 were determined and compared to the adsorbent ability of cellulose fibers, CF-8, and of a cellulose powder, CP-9. The results are shown in FIG. 4.

Figure 4:
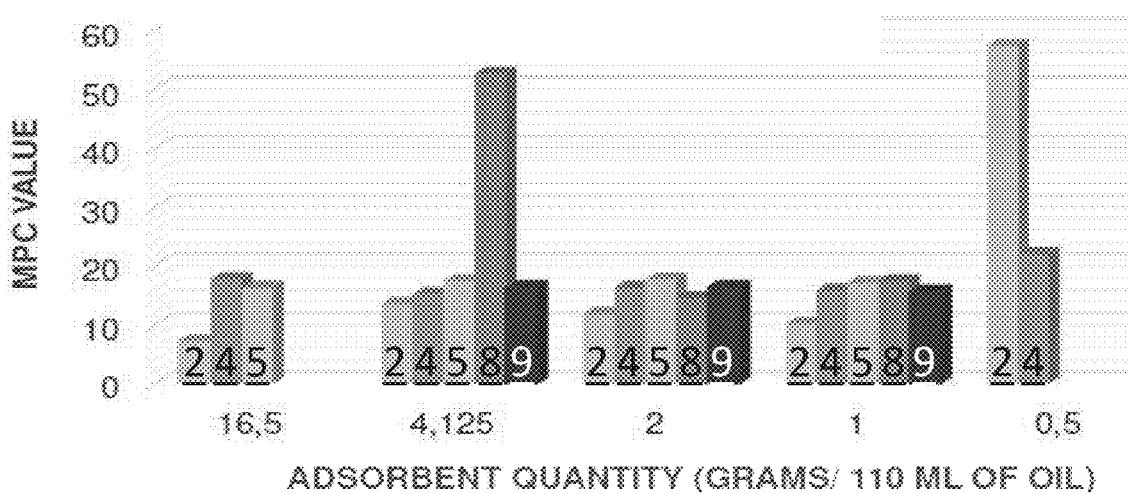
FIG. 4 is a graphical illustration of the membrane patch colorimetry (MPC) value with adsorbent quantity of Example 8.

FIG. 4 illustrates that the nonionic PSDVB-2 adsorbent having a surface area of 750 $m^2/g$ resulted in an increased removal ability of the degraded component of all of the adsorbents tested over all concentrations greater than 0.5 grams per 110 mL of oil.

Example 9: Effect of Cycling on Adsorbent Ability

Shell Turbo GT 32 oil having an initial MPC value of 56.5 dE was cycled through the PSDVB-2 of Example 2 to simulate a continuous cleaning of the oil. Specifically, 1,000 mL of the oil was adding to a 2,000 mL separating funnel. The funnel was located on top of a 2.54 centimeter diameter column packed with the adsorbent to a height of 4 centimeters. A 1,000 milliliter receiving flask was located under to column to collect the oil after is passed through the adsorbent. Once the oil had passed through the adsorbent, the collected sample was analyzed and then returned to the separating funnel for additional cycling through the adsorbent. The adsorbent was not changed between cycling. The MPC value of the oil after 20 cycles was 12.6. Qualitative membrane color analysis shows a significant reduction in the color until about the fourth cycle, after which the color did not significantly change indicating a stabilization in the MPC value and varnish removal.

Examples 10-11: Effect of Cycling Rate on Adsorbent Ability

The method of Example 9 was repeated with two different samples of shell Turbo GT 32 oil using different adsorbent materials in accordance with the method of Example 9, but using a flow rate of 362 and 730 milliliters per hour (mL/h), respectively. The results are shown in Table 3.

TABLE 3

| Example | 9 | 10 | 11 |
|---|---|---|---|
| Flow rate (mL/h) | 365 | 730 | 1,460 |
| MPC value (dE) | 8.5 | 9.5 | 12.6 |

Table 3 shows that increasing the flow results in a slight increase in the MPC value, but is still significantly reduced compared to the initial MPC value of 56.5 dE of the oil prior to introduction to the adsorbent.

Examples 12-14: Effect of Regeneration on Adsorbent Ability

The method of Example 9 was repeated three more times using a fresh adsorbent. After the 20 cycles, the adsorbents were regenerated in a 150 milliliter bottle of acetone, hexane, or petroleum ether, respectively. New samples of the shell Turbo GT 32 oil were then cycled through the respective regenerated adsorbents for 20 cycles and the MPC values determined. The results are shown in Table 4.

TABLE 4

| Example | 12 | 13 | 14 |
|---|---|---|---|
| Regeneration solvent | Acetone | Hexane | Petroleum Ether |
| MPC value (dE) | 6.5 | 14.6 | 9.3 |

Table 3 shows that the adsorbent ability of the regenerated adsorbents was similar to that of the initial adsorbent.

Example 15: Effect of Adsorbent on Additives

The method of Example 9 was repeated using a fresh adsorbent and the amounts of remaining antioxidant additives present in the oil before and after cycling were determined using the RULER method. The RULER method, which stands for Routine Useful Life Evaluation Routine by Linear Sweep Voltammetry, was performed according to ASTM D2272-14a. This method analyses the amount of antioxidants remaining in the oil compared to antioxidants level in the unused oil. The results are shown in Table 5 in percent change relative to the amount initial oil that was not yet cycled.

TABLE 5

| Example | 15-initial | 15-after cycling |
|---|---|---|
| Amine amount (%) | 42 | 75 |
| Phenol amount (%) | 1 | 14 |

Table 5 shows that the amount of both the amine and the phenol levels increased in the treated oil relative to the reference oil. This result is surprising and beneficial to the purified oil.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

The terms "a" and "an" do not denote a limitation of quantity, but rather denote the presence of at least one of the referenced item. The term "or" means "and/or" unless clearly indicated otherwise by context. Reference throughout the specification to "an aspect", "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments.

When an element such as a layer, film, region, or substrate is referred to as being "on" another element, it can be directly on the other element or intervening elements may also be present. In contrast, when an element is referred to as being "directly on" another element, there are no intervening elements present.

Unless specified to the contrary herein, all test standards are the most recent standard in effect as of the filing date of this application, or, if priority is claimed, the filing date of the earliest priority application in which the test standard appears.

The endpoints of all ranges directed to the same component or property are inclusive of the endpoints, are independently combinable, and include all intermediate points and ranges. For example, ranges of "up to 25 wt %, or 5 to 20 wt %" is inclusive of the endpoints and all intermediate values of the ranges of "5 to 25 wt %," such as 10 to 23 wt %, etc.

The terms "first," "second," and the like, "primary," "secondary," and the like, as used herein do not necessarily denote any order, quantity, or importance, but rather are used to help distinguish one element from another.

The term "combinations comprising at least one of the foregoing" or "at least one of" means that the list is inclusive of each element individually, as well as combinations of two or more elements of the list, and combinations of at least one element of the list with like elements not named. Also, the term "combination" is inclusive of blends, mixtures, alloys, reaction products, and the like.

Unless defined otherwise, technical and scientific terms used herein have the same meaning as is commonly understood by one of skill in the art to which this invention belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of removing a degraded component from a hydrocarbon fluid, the method comprising:
   receiving the hydrocarbon fluid from a fluid source;
   directing the hydrocarbon fluid to a first filter section containing a first porous medium capable of adsorbing the degraded component to produce a purified fluid that has a reduced amount of degraded component as compared to the hydrocarbon fluid;
   removing the purified fluid from the first porous medium;
   stopping directing the hydrocarbon fluid to the first porous medium;
   after stopping, directing the hydrocarbon fluid to a second filter section containing a second porous medium capable of adsorbing the degraded component to produce the purified fluid; and
   directing a flow of regenerant that is different than the purified fluid or the hydrocarbon fluid through the first filter section while directing the hydrocarbon fluid to the second filter section, to regenerate the first porous medium in the first filter section;
   wherein the regenerant is one of: acetone, methanol, ethanol, propanol, butanol, methyl acetate, ethyl acetate, a terpene, acetonitrile, dioxane, acetic acid, formic acid, chloroform, tetrahydrofuran, dimethylformamide, dimethyl sulfoxide, methyl ethyl ketone (MEK), methyl propyl ketone, methyl iso-amyl ketone, methyl iso-butyl ketone (MIBK), methyl oleate, methyl propyl ketone, n-methyl-2-pyrrolidone (NMP), n-propyl acetate, n-propyl propanoate, propylene glycol monobutyl ether, propylene glycol monoethylene ether acetate, propylene glycol monomethyl ether acetate, toluene, xylene, benzene, iso-pentyl acetate, iso-pentyl alcohol, iso-butyl isobutyrate, n-amyl acetate, n-amyl alcohol, benzyl alcohol, N—N-dimethyl formamide (DMF), n-propyl acetate, n-propyl propanoate, sulfolane, 1-nitro propane, sec-butyl acetate, methyl cellosolve, methyl carbitol, or methyl iso-butyl carbinol.

2. The method of claim 1, wherein the flow of the hydrocarbon fluid stream to the first filter section is stopped after an amount of time;
   wherein the regenerating the first porous medium comprises introducing the regenerant to the first filter section to remove an amount of the degraded component from the first porous medium.

3. The method of claim 2, wherein the introducing the regenerant to the first filter section comprises directing a first regenerant stream comprising the regenerant to the first filter section and removing a degraded component removal stream from the first filter section.

4. The method of claim 3, further comprising stopping the flow of the regenerant stream to the first filter section after an amount of the degraded component is removed from the first filter section and then re-initiating a flow of the hydrocarbon fluid stream to the first filter section to produce the purified stream.

5. The method of claim 2, further comprising:
   stopping a flow of the hydrocarbon fluid stream to the second filter section and directing the hydrocarbon fluid stream to a third filter section comprising a third porous medium capable of adsorbing the degraded component to produce the purified stream; and
   after stopping the flow of the hydrocarbon fluid stream to the second filter section, directing a second regenerant stream to the second filter section to remove the degraded component from the second porous medium.

6. The method of claim 2, wherein the introducing regenerant to the first porous medium further comprises removing the first porous medium located in a first filter location and introducing the regenerant to the first porous medium in a second location different from the first location; and
   the method further comprising: replacing the first porous medium to the first filter location after the amount of the degraded component is removed from the first porous medium.

7. The method of claim 2, wherein the first porous medium and the second porous medium each independently have a porosity and wherein the first porous medium and the second porous medium each independently comprise at least one of cotton, activated carbon, a zeolite, or a crosslinked polymeric material.

8. The method of claim 2, further comprising a solid particulate prefilter located upstream of at least one of the first porous medium or the second porous medium.

9. The method of claim 2, wherein at least one of the first porous medium or the second porous medium comprises a crosslinked polystyrene having:
a BET pore volume of greater than or equal to 0.6 mL/g; and
a surface area of 500 to 900 $m^2/g$, or 500 to 850 $m^2/g$ as determined in accordance with to ISO 9277:2010.

10. The method of claim 2, wherein at least one of the first porous medium or the second porous medium is non-ionic and is free of both a cationic and an anionic functionality.

11. The method of claim 2, wherein at least one of the first porous medium or the second porous medium has an average pore size of 5 to 18 nanometers.

12. A facility for removing a degraded component from a hydrocarbon fluid, the facility comprising:
a first filter section in fluid communication with a hydrocarbon fluid stream for receiving the hydrocarbon fluid and creating a purified hydrocarbon fluid;
wherein the first filter section comprises a first porous medium capable of removing a degraded component from the hydrocarbon fluid to create the purified hydrocarbon fluid; and
a second filter section in fluid communication with a regenerant stream receiving a regenerant that is different than the purified hydrocarbon fluid for removing a degraded component while the hydrocarbon fluid stream is passing through the first filter section;
wherein the regenerant is one of: acetone, methanol, ethanol, propanol, butanol, methyl acetate, ethyl acetate, a terpene, acetonitrile, dioxane, acetic acid, formic acid, chloroform, tetrahydrofuran, dimethylformamide, dimethyl sulfoxide, methyl ethyl ketone (MEK), methyl propyl ketone, methyl iso-amyl ketone, methyl iso-butyl ketone (MIBK), methyl oleate, methyl propyl ketone, n-methyl-2-pyrrolidone (NMP), n-propyl acetate, n-propyl propanoate, propylene glycol monobutyl ether, propylene glycol monoethylene ether acetate, propylene glycol monomethyl ether acetate, toluene, xylene, benzene, iso-pentyl acetate, iso-pentyl alcohol, iso-butyl isobutyrate, n-amyl acetate, n-amyl alcohol, benzyl alcohol, N—N-dimethyl formamide (DMF), n-propyl acetate, n-propyl propanoate, sulfolane, 1-nitro propane, sec-butyl acetate, methyl cellosolve, methyl carbitol, or methyl iso-butyl carbinol.

13. The facility of claim 12, further comprising at least one of a filter section valve capable of diverting a flow of the hydrocarbon stream between the first filter section and the second filter section or a regenerant direction valve capable of diverting a flow of the regenerant stream between the first filter section and the second filter section.

14. The facility of claim 12, further comprising a third filter section in fluid communication with the hydrocarbon fluid stream for receiving the hydrocarbon fluid and the purified stream for removing the purified hydrocarbon fluid; wherein the third filter section comprises a third porous medium capable of removing a degraded component from the hydrocarbon fluid.

* * * * *